(12) United States Patent
Reimels (10) Patent No.: US 10,285,747 B2
(45) Date of Patent: May 14, 2019

(54) IMPLANT DEPLOYMENT SYSTEM AND METHODS OF USE

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 413 days.

(21) Appl. No.: 13/644,376

(22) Filed: Oct. 4, 2012

(65) Prior Publication Data
US 2014/0100581 A1    Apr. 10, 2014

Related U.S. Application Data

(63) Continuation-in-part of application No. 12/456,602, filed on Jun. 18, 2009, now Pat. No. 8,657,832.

(60) Provisional application No. 61/132,499, filed on Jun. 18, 2008.

(51) Int. Cl.
*A61B 17/88* (2006.01)
*A61B 17/84* (2006.01)

(52) U.S. Cl.
CPC ........ *A61B 17/8858* (2013.01); *A61B 17/844* (2013.01)

(58) Field of Classification Search
CPC . A61B 17/3468; A61B 17/7065; A61B 17/88; A61F 2/46; A61F 2/468; A61F 2002/4624; A61F 2002/4623; A61F 2002/4627; A61F 2/95; A61F 2002/9517; A61F 2/966
USPC .......................................... 606/99
See application file for complete search history.

(56) References Cited

U.S. PATENT DOCUMENTS

| | | | | |
|---|---|---|---|---|
| 5,833,694 A | * | 11/1998 | Poncet | 623/1.11 |
| 5,885,299 A | * | 3/1999 | Winslow et al. | 606/99 |
| 6,402,760 B1 | * | 6/2002 | Fedida | 606/108 |
| 6,514,261 B1 | * | 2/2003 | Randall et al. | 606/108 |
| 2007/0233222 A1 | * | 10/2007 | Roeder et al. | 623/1.11 |
| 2008/0319524 A1 | * | 12/2008 | Yachia et al. | 623/1.11 |

* cited by examiner

*Primary Examiner* — Anu Ramana
(74) *Attorney, Agent, or Firm* — Honigman Miller Schwartz and Cohn LLP (57) ABSTRACT

A surgical implant deployment system for deploying and removing an implant into a vertebral body. Upon insertion of the implant into the vertebral body, the actuator handle is turned causing the actuation rod to expand or compress the implant.

15 Claims, 14 Drawing Sheets

4.5mm undeployed model 4.5mm deployed model 5.5mm undeployed model 5.5mm deployed model 7.0mm undeployed model 7.0mm deployed model

IMPLANT DEPLOYMENT SYSTEM AND METHODS OF USE

CROSS-REFERENCE TO RELATED APPLICATIONS

The present application is a continuation-in-part to U.S. patent application Ser. No. 12/456,602, filed Jun. 18, 2009, and which claims priority to U.S. Provisional Application Ser. No. 61/132,499, which was filed Jun. 18, 2008, all incorporated by reference in their entirety.

BACKGROUND

The invention generally relates to the field of spinal surgery. In particular, the present invention relates to the field of surgical access to the spine. More particularly, the present invention relates to systems and methods of deployment of an implant.

The spine is a series of individual bones called vertebrae, separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. The spine curves in at the lumbar region, back out at the thoracic region, and back in at the cervical region.

In some cases, a procedure known as vertebroplasty is used to treat compression fractures in the vertebra such as those caused by osteoporosis, cancer, or stress. Vertebroplasty is an image-guided minimally invasive non-surgical therapy for injecting an orthopedic cement mixture through a needle into the fractured bone. The mixture fills or substantially fills the cavity of the compression fracture and is limited to certain chemical compositions, thereby limiting the amount of otherwise beneficial compounds that can be added to the fracture zone to improve healing. In an alternative procedure known as kyphoplasty, a ballon is first inserted in the compression fracture and the vertebra is expanded before the cement is injected into the newly formed space. All of the above devices do not contain an implant that mechanically deforms in bone creating superior interdigitation and restore vertebral body height. However, these devices are readily available in prepackaged and sterilized form along with disposable instrumentation.

Examples of alternatives to the above devices may be found in U.S. Pat. Pub. No. 2008/0071356, entitled "Expandable Support Device and Method of Use" and incorporated herein by reference. However, the instrumentation and tools for these types of devices requires considerable amounts of force to deploy the devices. Cleaning and sterilization of the reusable instrumentation requires additional effort and time and may be costly over long periods of time. The instruments and methods of the present disclosure attempts to solve these problems as well as others.

SUMMARY OF THE INVENTION

Provided herein are systems, methods and compositions for an Implant Deployment system and methods of use. The implant deployment system generally comprises an actuation rod; an actuator handle coupled to the actuation rod; an inserter locking tube disposed over the actuation rod and coupled to an inserter handle; an energy storage container disposed at the distal end of the inserter locking tube; wherein upon insertion of the implant into the vertebral body using the inserter handle, the actuator handle is turned causing the energy storage container to release its energy and drive the actuation rod to expand or compress the implant disposed at a distal end of the inserter locking tube.

The method of using the implant deployment or redeployment comprising the steps: inserting the surgical implant insertion system into a patient; releasing the energy from the energy storage container; wherein the released energy drives the actuation rod which expands and deploys the implant.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 1:
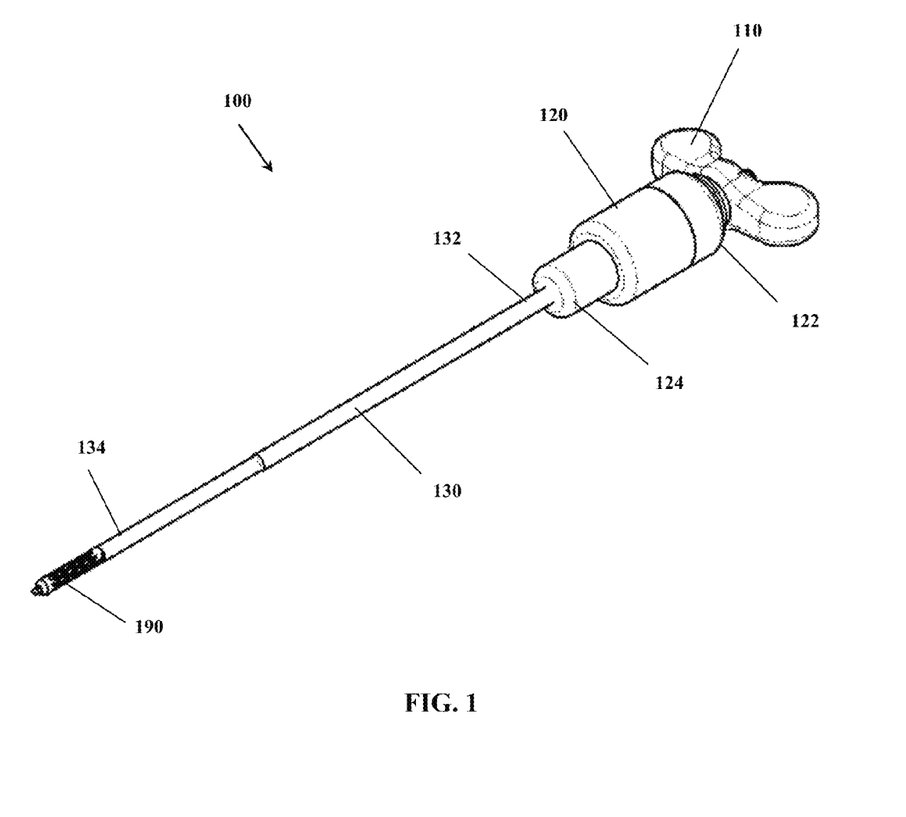
FIG. 1 is a perspective view of the implant deployment system.

As shown in FIG. 1, the implant deployment system 100 comprises a handle 110 operably coupled to an energy storage canister 120, a cannula 130 including a proximal end 132 and a distal end 134, and an implant 190 operably coupled to the distal end 134 of the cannula 130. The implant deployment system 100 functions to deploy the implant 190 at a target location, expand the implant 190, and release the implant 190 at the target location. The handle 110 is turned to release the energy within the energy storage canister 120 to deploy the implant 190. The energy storage canister 120 contains a preloaded energy storage device. This energy storage canister allows the integration of all the delivery system components into one single use preassembled system.

The energy storage canister coupled with the implant deployment system 100 provides the necessary actuation compression force through the controlled release of a predetermined amount of stored energy within the canister 120. The source of this preloaded energy can be a compressed spring or a pressurized metal welded bellows. There are various types of applicable welded bellow devices that can produce linear or rotary motion from pressurized air. Welded bellows act as a flexible seal when designed as a mechanical feedthrough, allowing movement of a tool within a sealed environment under vacuum or positive pressure. Metal bellows are also used within a bearing housing to translate rotation from an input shaft to a co-linear output shaft while sealing hermetically, eliminating the need for a dynamic seal. Also, an exothermic chemical reaction can be used as a source of preloaded energy. One example of such a chemical is sodium azide, used in airbags. When it is heated, it quickly generates energy and produces gas which can be used to drive the actuation rod.

The release of stored energy requires much less mass than a comparable energy generation systems and can be made from inexpensive plastic and metal materials due to the lower stress on active components. The energy storage container can also be detachable and reusable to further save on cost.

Figure 2:
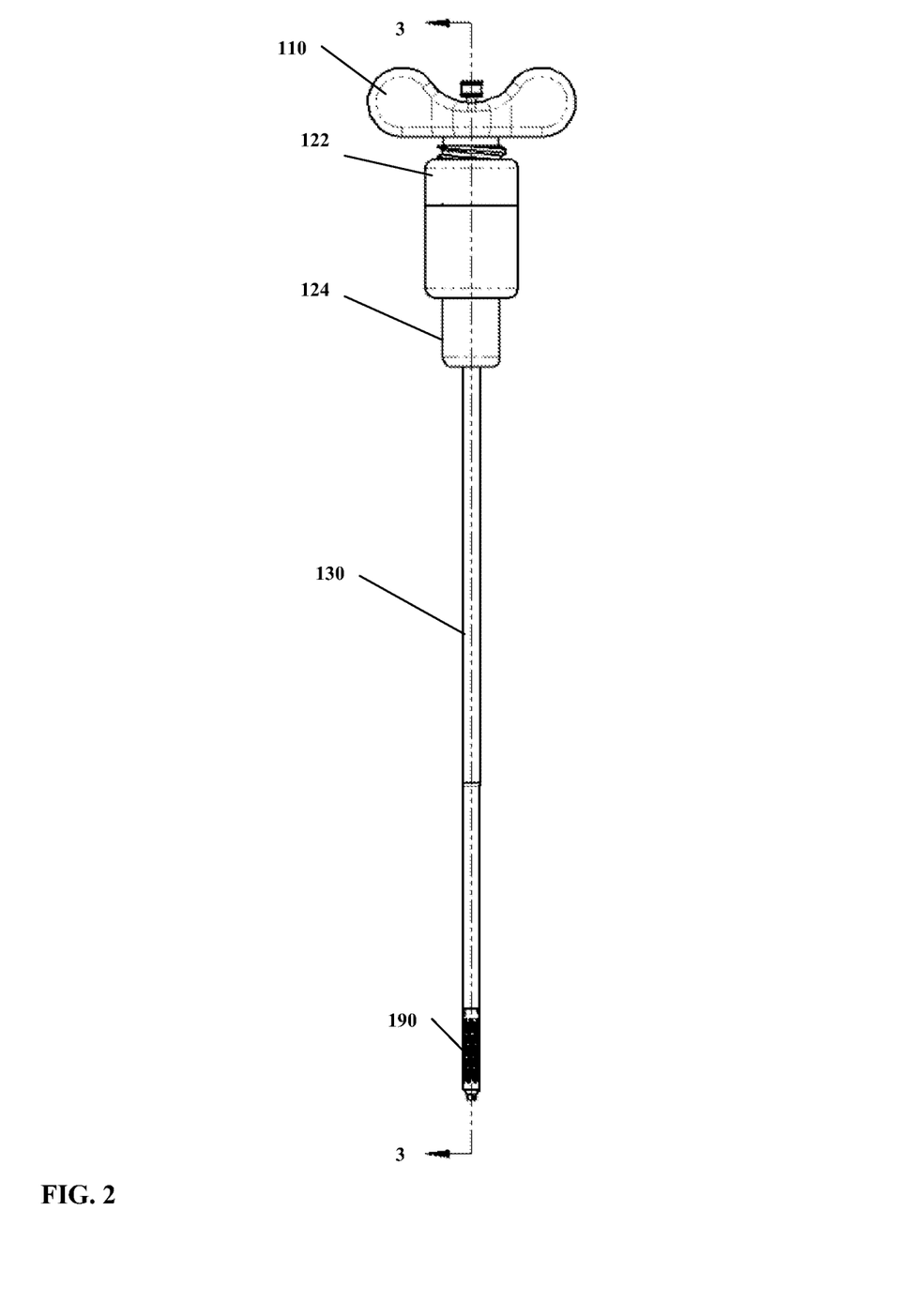
FIG. 2 is a side view of the implant deployment system.
Figure 3:
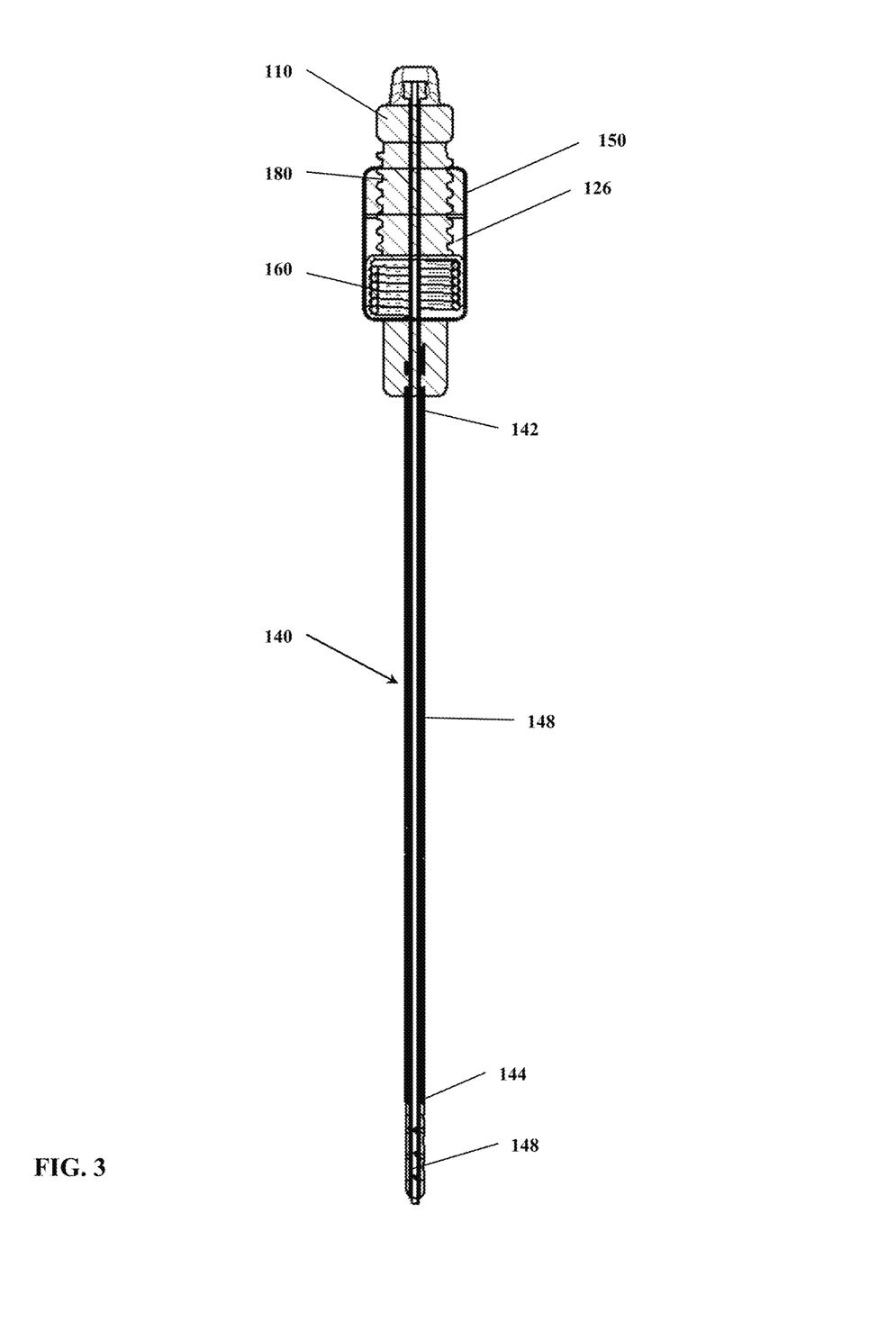
FIG. 3 is a cross-sectional view of the implant deployment system taken along lines 3-3 from FIG. 2.

As shown in FIGS. 1-3, the energy storage canister 120 includes a proximal section 122 and a distal section 124 with a central lumen 126 traversing the proximal end 122 and the distal end 124. An actuator rod 140 is operably coupled to the distal section 124 of the energy storage canister 120. The actuator rod 140 includes a proximal section 142 and a distal section 144 and a central shaft 148 through which a central lumen 146 is disposed therein. The central lumen 146 of the actuator rod 140 is in fluid communication with the central lumen 126 of the energy storage canister 120 may be in fluid communication with a plurality of fenestration holes 148 on the distal section 144 of the actuator rod 140.

Figure 4:
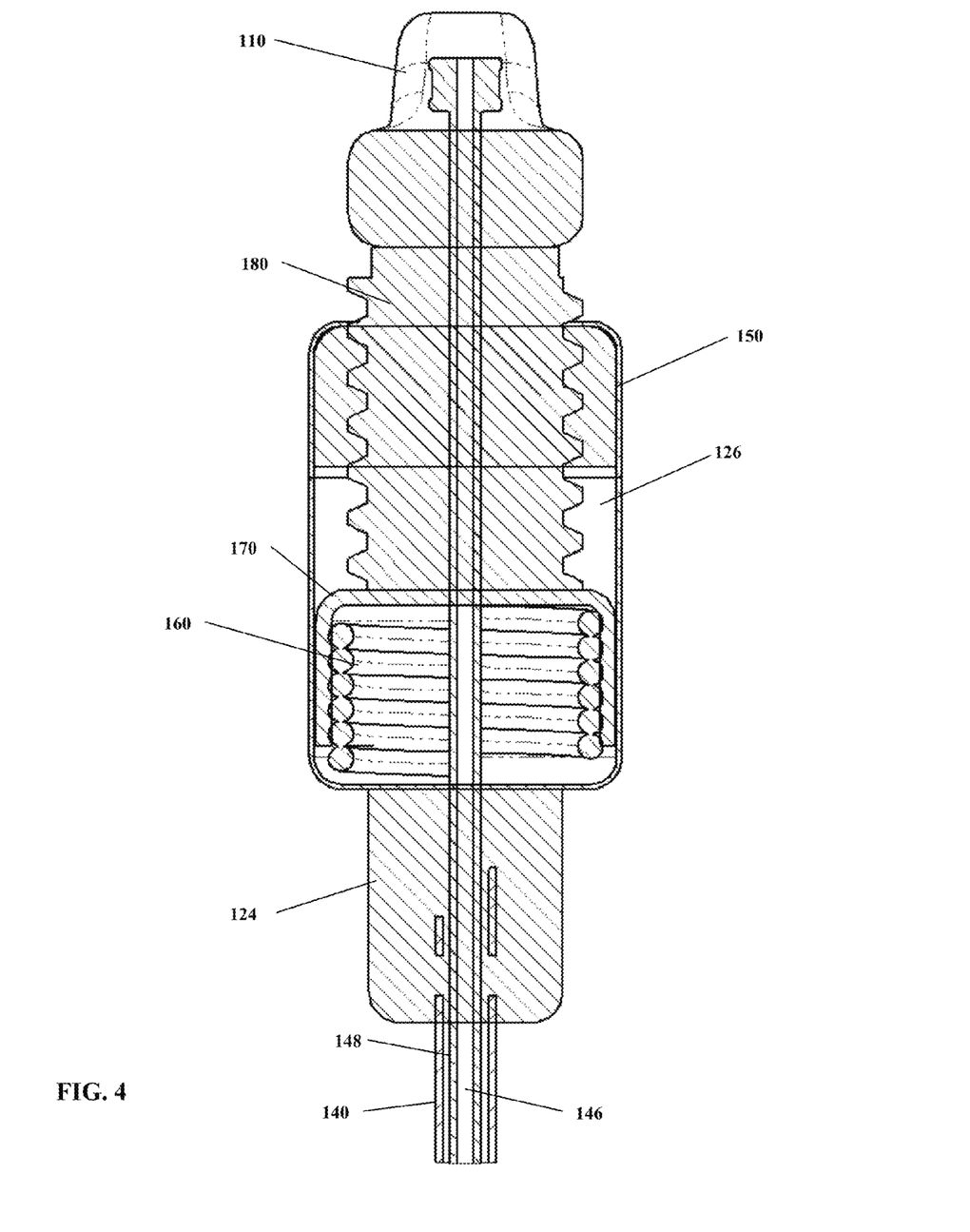
FIG. 4 is an enlarged cross-sectional view of the energy storage canister.

As shown in FIGS. 3-4, the energy storage canister 120 includes a stamped steel housing 150 including a compressed spring 160 operably coupled with a piston 170 and an energy release screw 180. The spring 160 is coaxially disposed within the piston 170 and coaxially coupled with the energy release screw 180. The energy release screw 180 is operably coupled with the handle 110. The energy release screw 180 may be a low friction plastic screw of sufficient diameter that is used to control the release of the actuation force of the compressed spring 160 operably coupled to the actuator rod 140. In one embodiment, the actuator rod 140 moves along the longitudinal axis of the implant deployment system 100 to deploy the implant 190 located on the distal end of the actuator rod. In other embodiment, the actuator rod 140 may move a longitudinal distance between 1.0 mm and 10.0 mm to deploy the implant.

Figure 12:
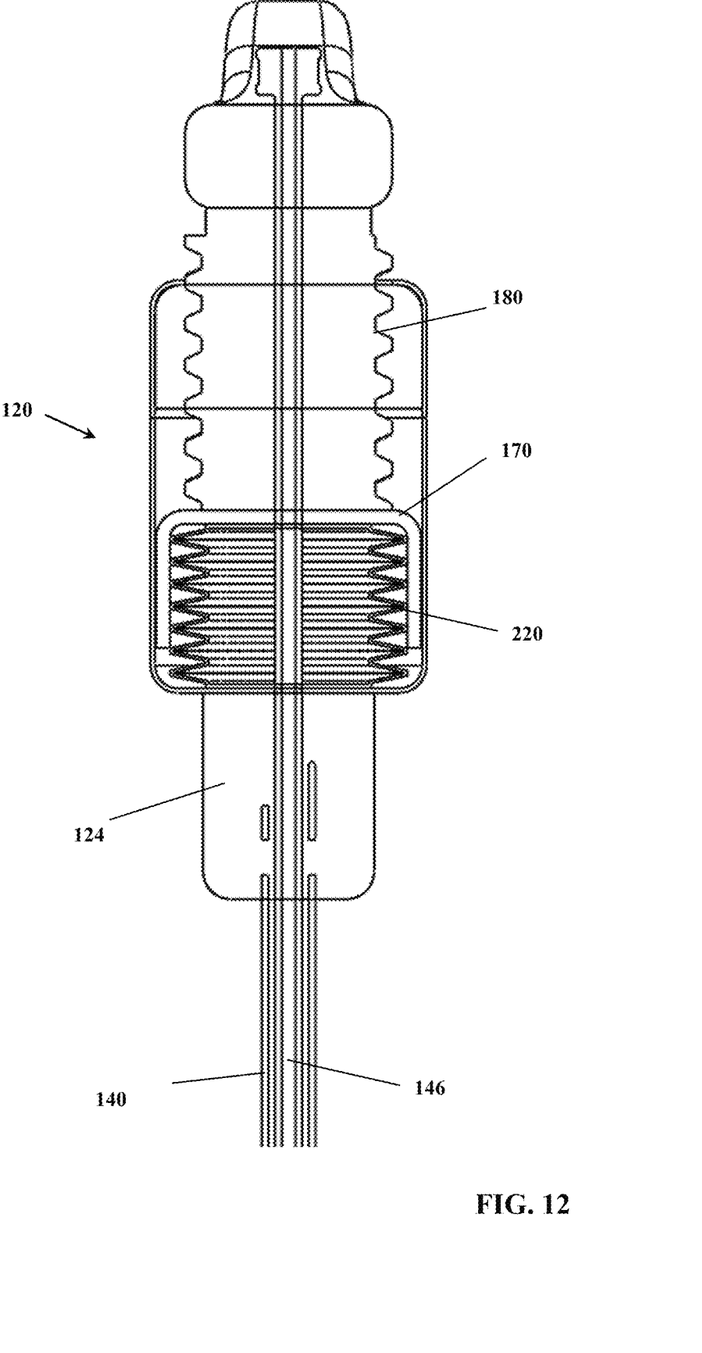
FIG. 12 is cross-sectional view of an alternative embodiment with a welded bellow device for the energy storage container.

In an alternative embodiment, the energy storage container may contain flexible metal bellows. There are many bellows device known in the arts, but an exemplary bellows device is shown in FIG. 12, flexible metal bellows 220 are operably coupled to the energy storage container's body. The flexible metal bellows 220 are filled with compressed gas and contained within the piston 170 as to provide an expansion force as the release screw 180 is moved proximally, the flexible metal bellows 220 expand and move the piston 170 proximally and consequently the actuator rod 140 is pulled proximally to expand the implant.

Figure 13:
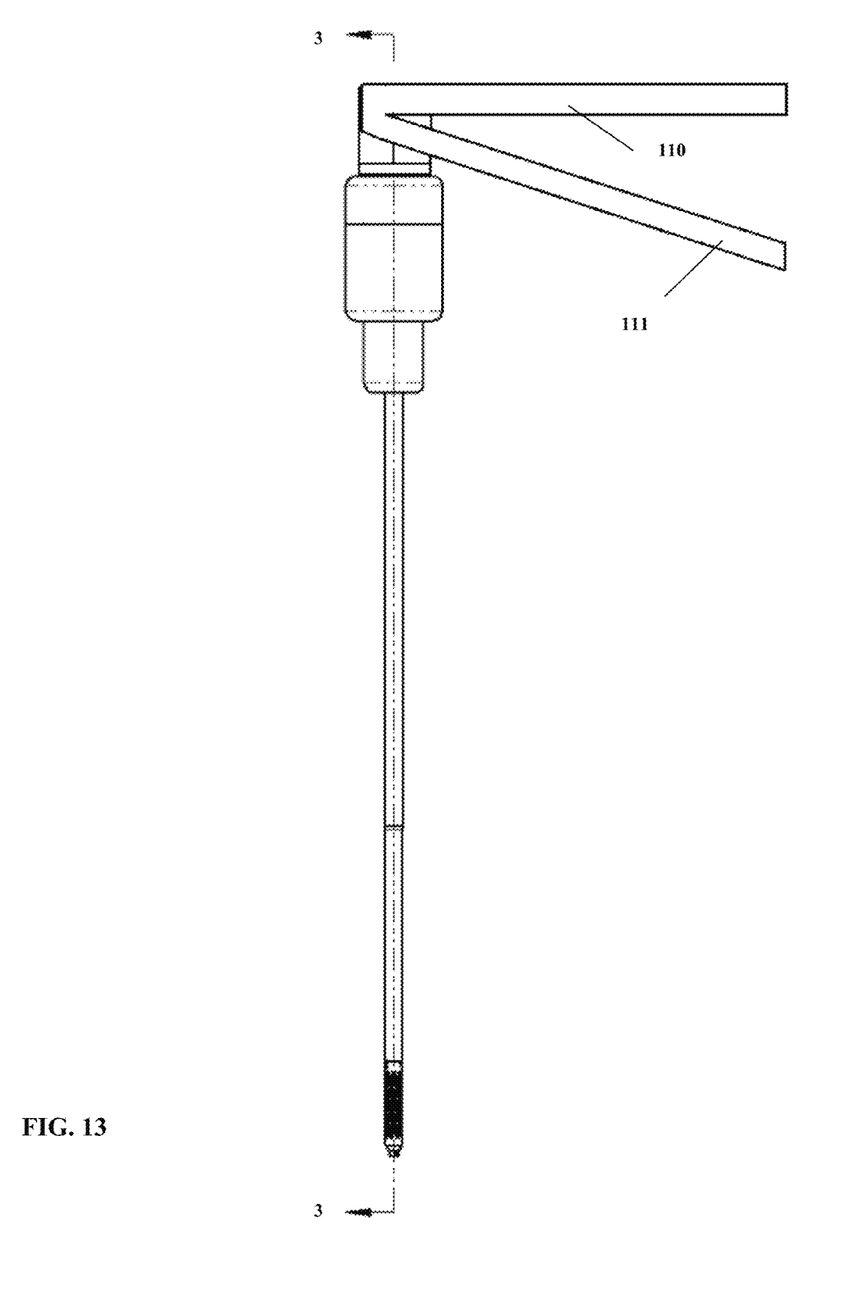
FIG. 13 is a perspective view of an alternative embodiment with a linear ratchet energy control release.

The implant deployment system includes the ability to release stored energy from the energy storage canister 120 in a controlled manner that governs the rate of longitudinal movement and provides discreet increments of longitudinal displacement. The method of energy release may be the energy release screw 180, the flexible metal bellows 220, or a linear ratchet mechanism similar to a come-along ratchet. While the the energy release screw is threaded, the linear ratchet mechanism has a linear rack with teeth, and a pivoting, spring-loaded finger called a pawl that engages the teeth. The linear ratchet mechanism is shown in FIGS. 13 and 14, and has teeth 182 that are uniform but asymmetrical, with each tooth having a moderate slope on one edge and a much steeper slope on the other edge.

Figure 11:
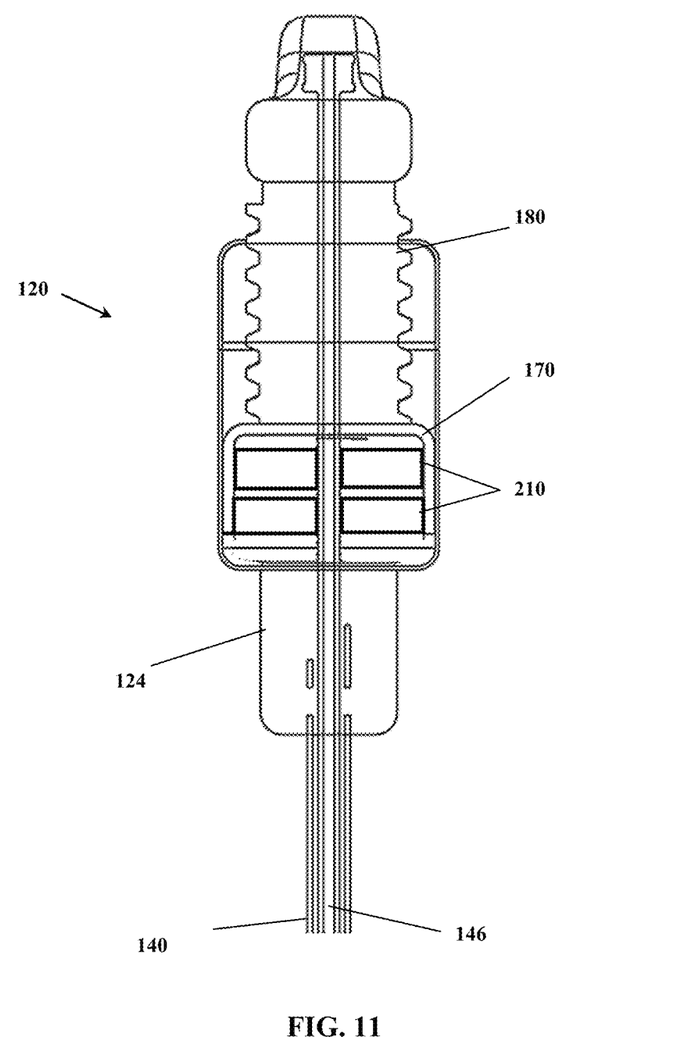
FIG. 11 is cross-sectional view of an alternative embodiment with the energy storage canister operably coupled with magnets.
Figure 14:
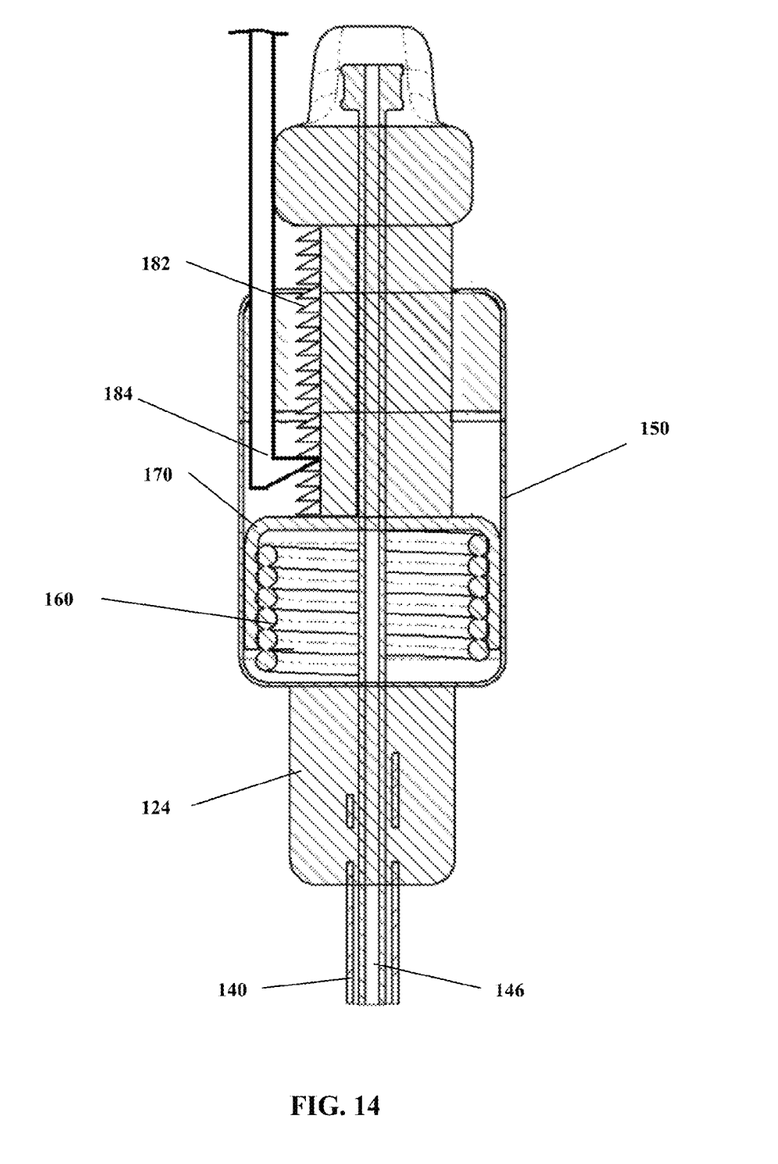
FIG. 14 is an enlarged cross-sectional view of an alternate embodiment of the energy storage canister

As shown in FIG. 14, when the teeth 182 are moving in the unrestricted, forward or distal, direction, the pawl 184 may slide up and over the sloped edges of the teeth 182, with a spring forcing it into the depression between the teeth 182 as it passes the tip of each tooth. When the teeth 182 move in the opposite, backward or proximal, direction, the pawl 184 will catch against the sloped edge of the first tooth it encounters, thereby locking it against the tooth and preventing any further motion in that direction. A trigger 111 can be combined with a handle 110 to release the pawl and allow the spring 160 to force the piston 170 proximally. The spring 160 is coaxially disposed within the piston 170 and coaxially coupled with the linear ratchet mechanism. The linear ratchet mechanism is operably coupled with the handle 110 and trigger 111. The handle 110 and trigger 111 are used to control the release of the actuation force of the compressed spring 160 operably coupled to the actuator rod 140 through the linear ratchet mechanism. Alternatively, the linear ratchet mechanism is operably coupled with the flexible metal bellows or the compressed spring. The linear ratchet mechanism when operably coupled with compressed gas of the flexible metal bellows or the compressed spring would cause the ratchet teeth to move proximally as the gas expands or the spring expands. Each trigger pull may be single ratchet tooth in proximal distance; alternatively, each trigger pull of the ratchet mechanism may be a plurality of ratchet teeth depending on the deployment desired for the implant. Alternative release mechanisms besides the release screw or the ratchet mechanism may include a friction brake system, a ratchet lever hoist system Alternatively, a bow mechanism, pressure-differential mechanism, a vacuum-plunger system, or the wobble plate system could also be used for the energy storage canister. Preferably, the energy storage canister stores potential energy in any shape or form. In one embodiment, the potential energy is in the form of a compressed spring, in other embodiments, the potential energy may be in the form of alternative elastic potential energy sources, such as a bow that is deformed under tension. The potential energy source is a consequence of a force that tries to restore the object to its original shape. Alternative potential energy sources may be electrostatic potential energy or magnetic potential energy. For example, as shown in FIG. 11, two magnets 210 facing the same poles are forced together within the piston 170, such that proximal movement of the release screw 180 will release the potential energy of the two magnets as to cause proximal movement of the distal section 124 and actuation rod 140. Alternatively, a bow mechanism can couple the piston 170 with a flexible material or string that is drawn back towards the distal section 124, whereby the flexible material or string is released by the release screw 180 to provide proximal movement of the distal section 124 and the actuation rod 140.

The release screw or ratchet mechanism could be attached to the energy canister by use of a linkage that could amplify or reduce the mechanical advantage to optimize the user interface. The release mechanism cannot be a valve or clamping mechanism that would allow uncontrolled motion.

Figure 5:
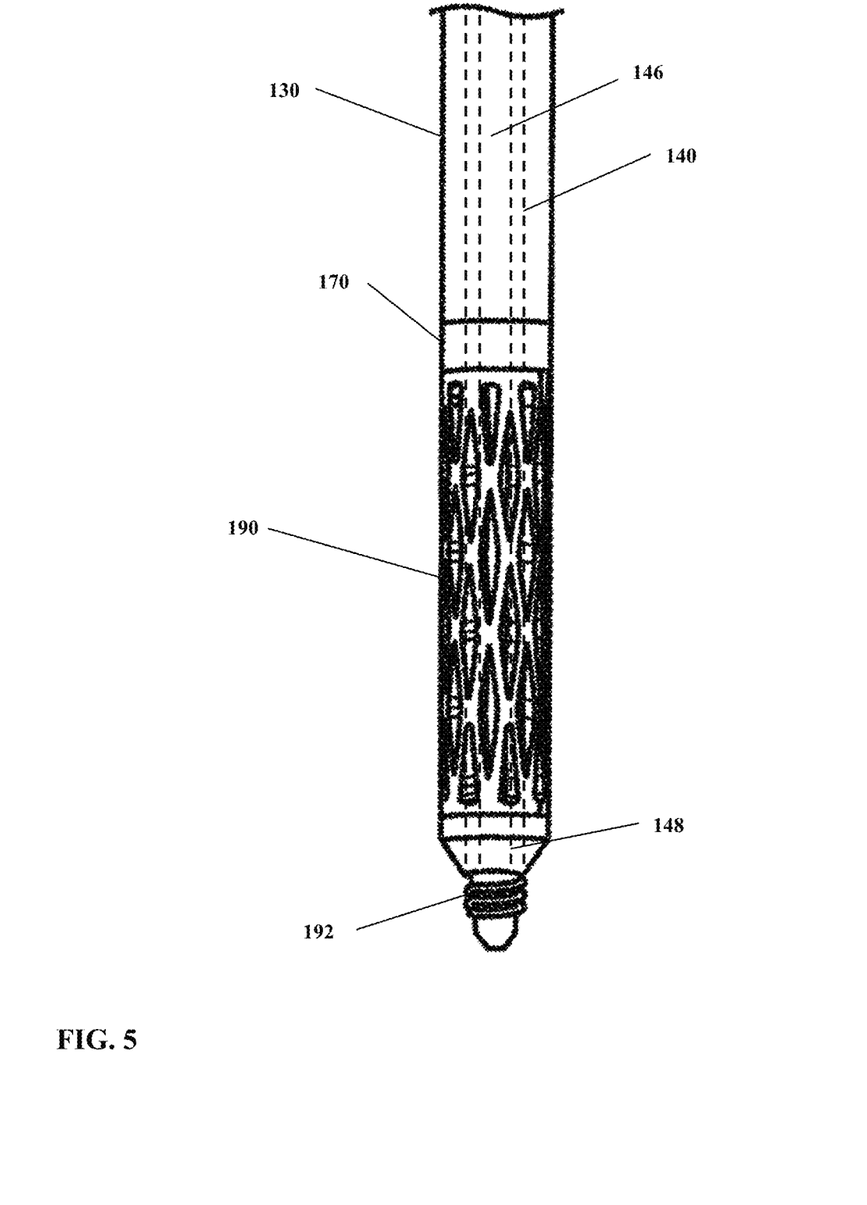
FIG. 5 is an enlarged cross-sectional view of the distal end of the implant deployment system.
Figure 6:
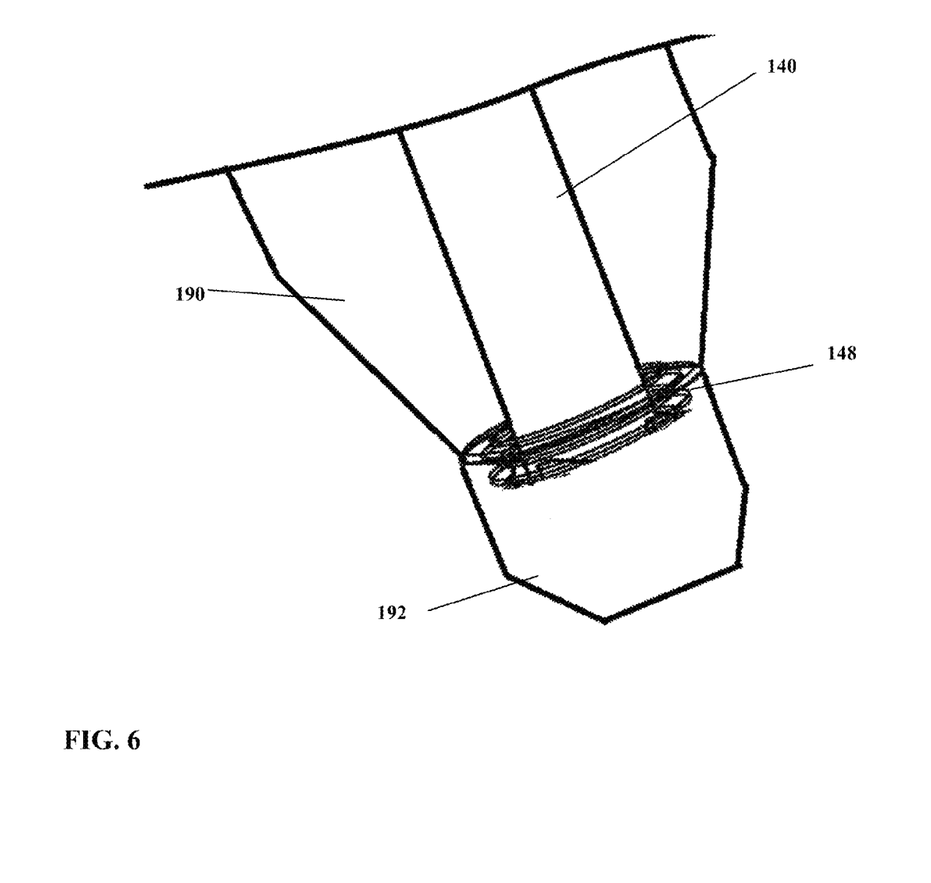
FIG. 6 is an enlarged perspective view of the distal end of the actuation rod coupled with the distal end of the implant with a locking mechanism.

To maintain the interface between the implant 190 and inserter cannula 130, a coupling mechanism 148 may be employed on the distal end of the actuation rod 140, as shown in FIGS. 5-6. The coupling mechanism 148 could be a threaded connection between the distal end of the implant 190 and the distal end of the actuation rod 140, as shown in FIG. 6. In one embodiment, the threaded connection of the coupling mechanism may be a quarter turn, in other embodiments, it may be a half-turn, a three-quarters turn, or a threaded turn between a quarter and two turns. The number of turns for the threaded connection may be adjusted for a quick release or disengagement of the actuation rod with the implant depending on the type of implant and disengagement desired. The interface between the implant and delivery system could alternatively be an interconnect based on a bayonet or Y-turn coupling mechanism. A bayonet coupling mechanism has one or more "L" shaped cutouts or slots on the female side and a corresponding number of radial pins on the male side. The slots are shaped like a capital letter "L" with a "serif", a short upward segment at the end of the horizontal arm; the pin slides into the vertical arm of the L, rotates across the horizontal arm, then is pushed slightly upwards into the short vertical serif by the spring; the connector is no longer free to rotate unless pushed down against the spring until the pin is out of the serif.

To couple the two parts, the pin(s) on the male are aligned with the slot(s) on the female and the two pushed together. Once the pins reach the bottom of the slot, one or both parts are rotated so that the pin slides along the horizontal arm of the L until it reaches the "serif". The spring then pushes the male connector up into the "serif" to keep the pin locked into place. A user can connect them quickly and, unlike screw connectors, they are not subject to cross-threading. To disconnect, the two parts are pushed together to move the pin out of the "serif" while twisting in the opposite direction than for connecting, and then pulling apart.

Also, other types of locking mechanisms are possible such as Y-turn, "J" shaped, saw-tooth, and other quarter turn systems know in the art. Both the screw and the locking mechanism can be designed to be either the male or female side. Examples of these designs are show in FIGS. 9 and 10.

As shown in FIGS. 3-4, the energy storage canister 120 controls the release of stored energy and allows the use of lighter weight less expensive materials. The energy storage canister can be directly assembled to the implant inserter cannula 130 and actuation rod 140. The energy storage canister 120 would be assembled using a compressed spring or charged bellows and then locked in place by an energy release screw 180 mechanism. The actuation rod 140 is operably coupled to the piston 170 that forms the connection between the energy release canister 120 and release screw 180 so the longitudinal movement of the piston 170 is directly transmitted to the actuation rod 140. The actuation rod 140 could be pre-tensioned so the implant 190 is pre-stressed before implant deployment occurs. The pre-stress or pre-tension eliminates corollary movement or incidental force in the system, so the release of the energy from the canister is more efficient. The pre-stress also eliminate the need for a proximal threaded connection between the Implant and the distal section of the inserter cannula 130. The elimination of the proximal thread on the implant reduces additional modification to the implant for deployment. The high energy storage canister can be made from stamped and drawn metal materials.

The energy storage canister 120 includes a load versus displacement curve, since the largest actuation force occurs at zero displacement. In one embodiment, the implant 190 may require a large initial compression force to begin the buckling of the implant to start the expansion process. Once buckling is initiated, further expansion requires less force as the angle of the displaced struts increases. The size of the energy storage canister can be adjusted to compensate for the largest actuation force necessary at zero displacement. The implant deployment system may be fully integrated with each implant, allowing direct delivery of the implant with no assembly in the operation room. Since the force required to undeploy and collapse the implant is much less than the initial actuation force, the implant deployment system could be used to reduce implant diameter by turning the energy release screw 180 in the opposite direction. In one embodiment, the energy storage canister must be capable of storing enough energy to produce a 4000 N initial force to buckle the implant. In other embodiments, the initial force may be between about 10 N to 10,000 N, alternatively, between about 40 and 8,000 N, alternatively, between about 100 and 6,000 N, alternatively, between about 400 and 4,000 N. The storage canister must be capable of delivering sufficient force to allow full expansion of the Implant over 4 mm of travel.

In one embodiment, the actuation rod 140 could be cannulated including a central lumen 146 for employing a smaller diameter wire, as shown in FIGS. 4-5. In one embodiment, the central lumen of the actuation rod 140 may accommodate a K-wire, which may eliminate the need to thread the actuator rod 140 down through the implant after removal of the K-wire. The actuator rod 140 would either be removed for cement delivery or the cannulation provides a lumen for cement delivery. The actuation rod 140 combined with fenestration at the distal end could be used to allow the delivery of cement through the delivery system without having to remove any instrumentation prior to cement delivery. The use of a cannulated actuator rod eliminates the need to connect the actuator rod separately after delivery over a K-Wire.

The storage energy canister should be made from rigid stable material such as metal that does not age or lose mechanical properties over time. Inexpensive welded bellows are available that could be hermetically sealed and would thus allow the storage of compressed gas over long periods of time. Spring assemblies using inner and outer call springs could be compressed well within their elastic range eliminating any potential relaxation over time. The storage canister must be made from strong stable material that will not degrade during sterilization.

Having the delivery mechanism pre-attached to the implant eliminates the need for individual coupling mechanisms between the components. The cannulated actuator rod also allows the pre-tensioning of the system to make the transfer of energy to the Implant more efficient.

The implant deployment system may be made of disposable material and may be coupled with single use drills and cannulas. If the cannulated actuator rod is used for cement delivery, the use of a fully integrated system would allow the tailoring of the deployment travel to ensure each implant can be fully deployed. The use of a pre-assembled single use delivery system eliminates the need for a separate locking mechanism for the Implant.

Figure 7:
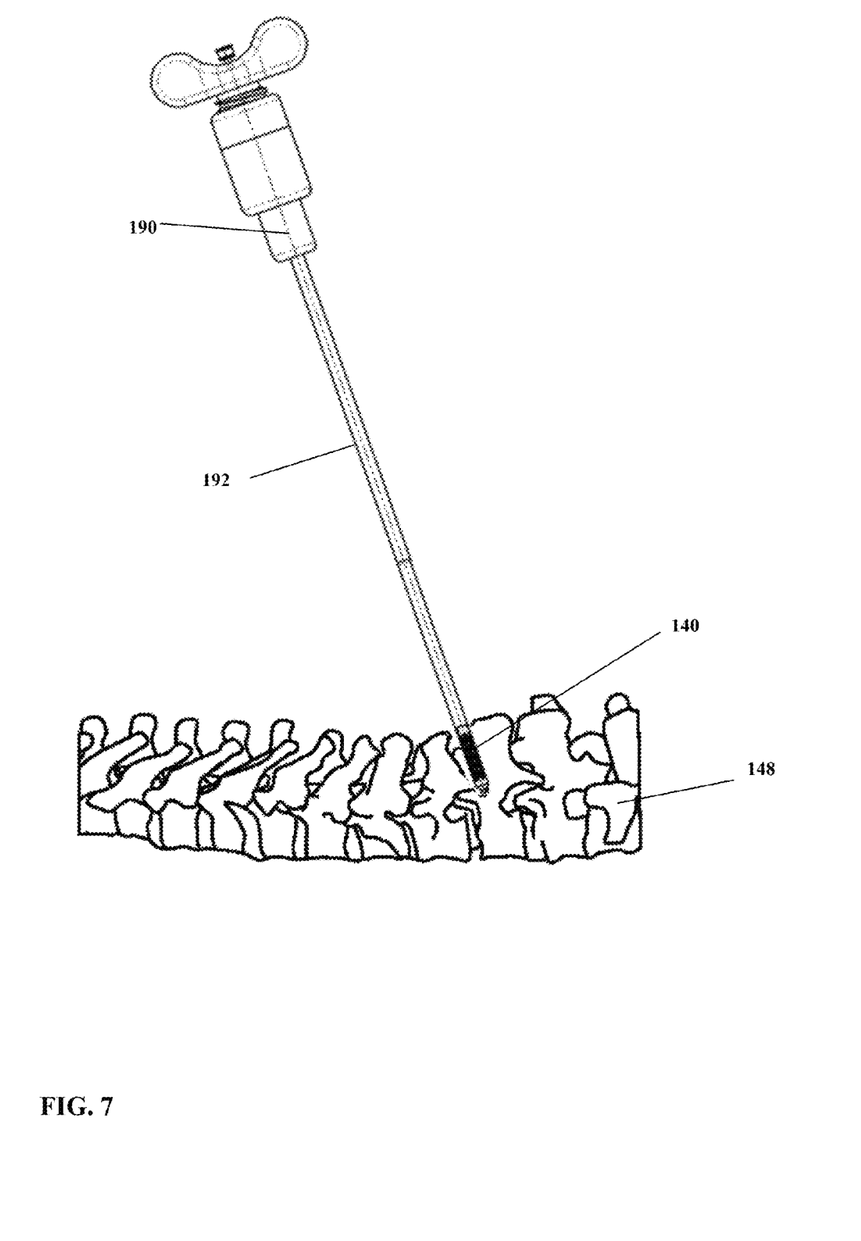
FIG. 7 is a side view of the implant deployment system being deployed into a vertebrae.
Figure 8:
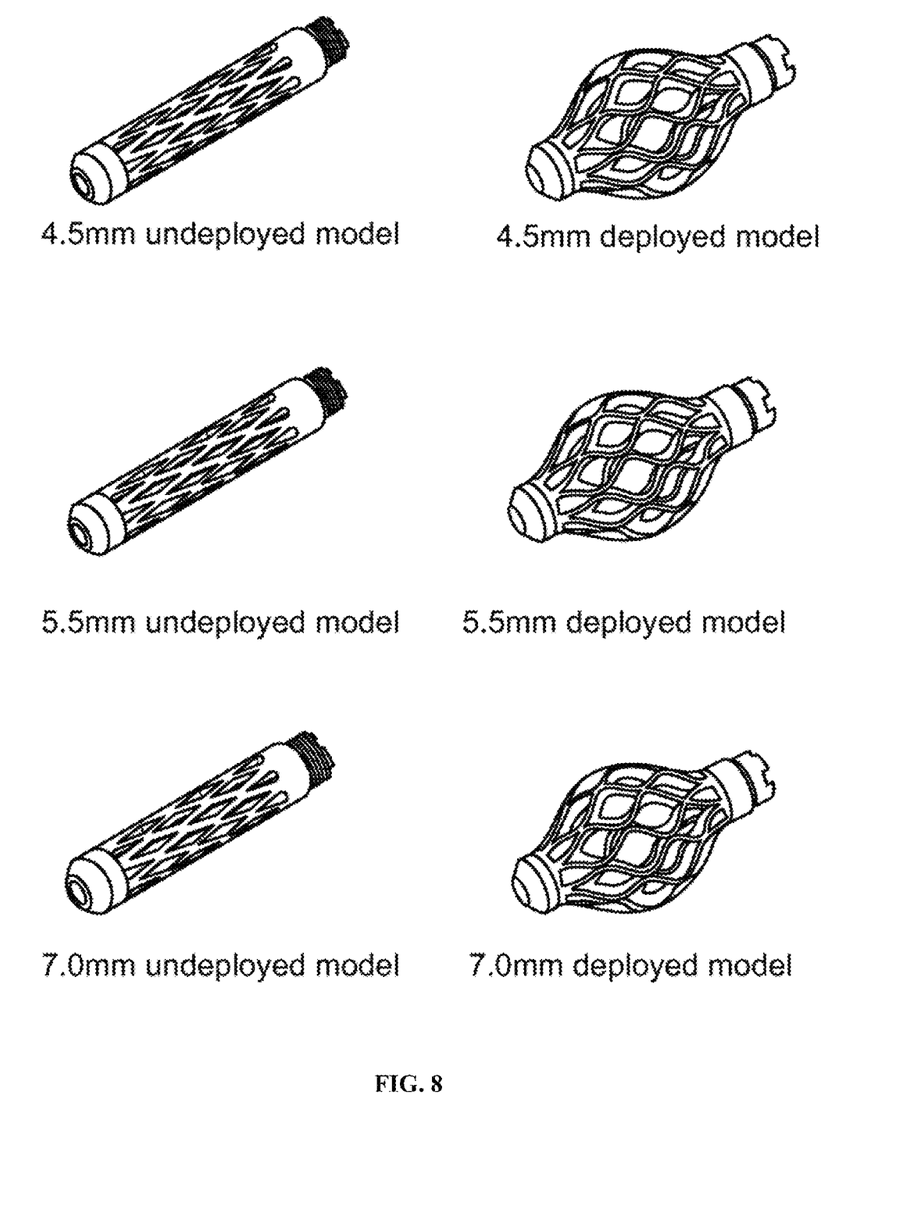
FIG. 8 is of perspective views of various implants in undeployed and deployed states.
Figure 9A:
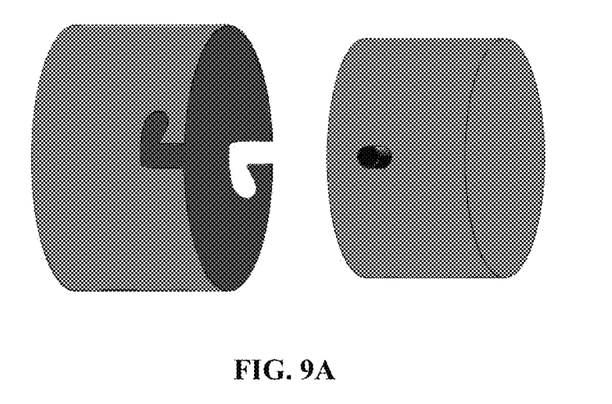
FIGS. 9A-9C are various types of coupling mechanisms.
Figure 9B:
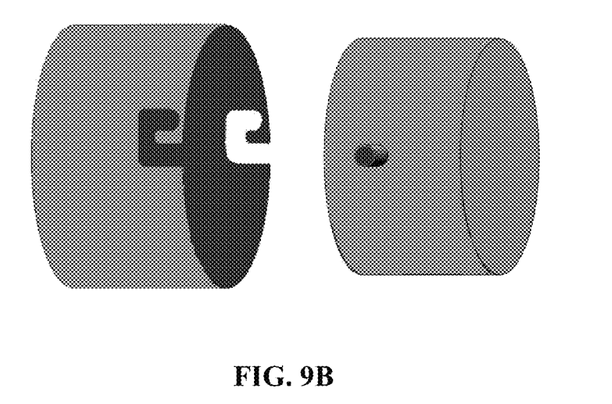
Figure 9C:
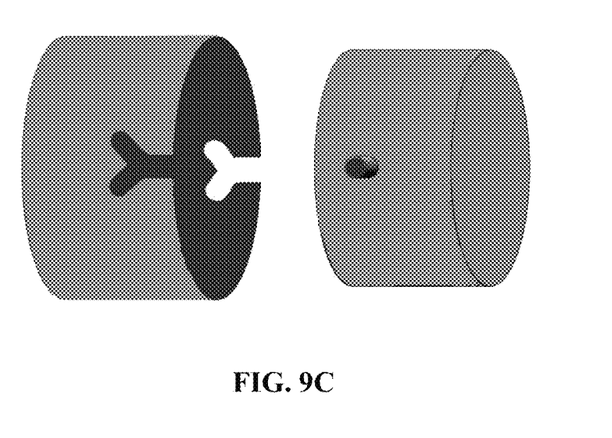
Figure 10A:
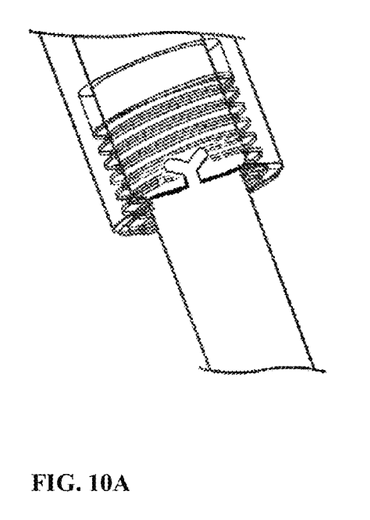
FIGS. 10A-10D are exemplary views of an implant coupling mechanisms.
Figure 10B:
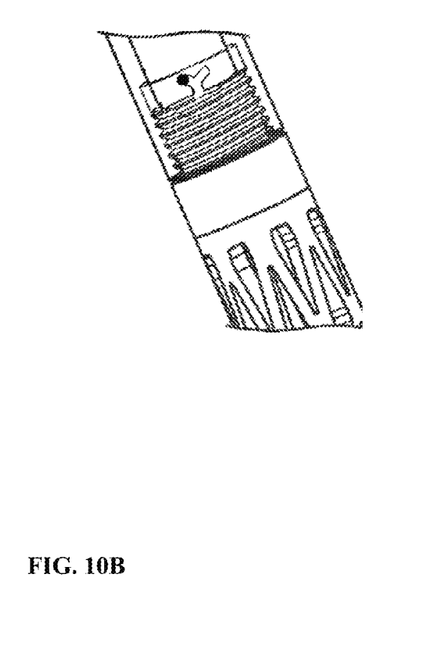
Figure 10C:
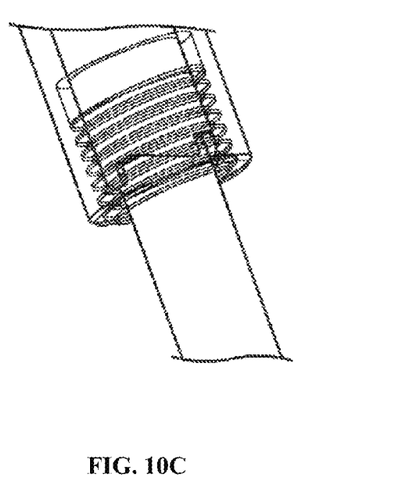
Figure 10D:
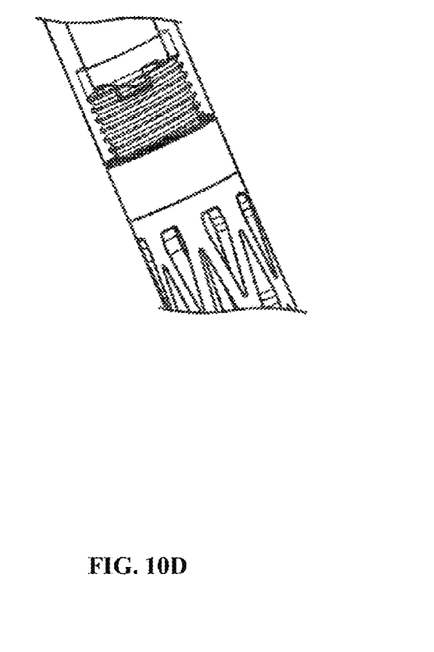

FIG. 7 shows implant deployment into a vertebra. While referencing fluoroscopic imaging in the lateral plane, the handle is rotated in a clockwise direction to deploy the implant. The red band on the actuator will become visible as the actuator is rotated and the implant is deployed. Once the desired degree of implant deployment has been achieved stop rotating the handle. A stop mechanism has been built into the actuator to prevent overdeployment of the implant.

An exemplary cement delivery procedure includes using a PMMA bone cement that is mixed in accordance with packaging or other instructions with the bone cement. Once the cement has been mixed to the desired consistency, the implant deployment system is disengaged from the implant and the implant is deployed. Then, a desired amount of cement is injected into the implant. The cement delivery can be verified under live fluoroscopy. The implant deployment can be then be removed from the implant.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A surgical implant insertion system for deployment and removal of an implant into a vertebral body, comprising:
    an actuation rod;
    an actuator handle coupled to the actuation rod;
    an inserter locking tube disposed over the actuation rod and coupled to an inserter handle;
    an energy storage container coupled with the inserter locking tube;
    wherein upon insertion of the implant into the vertebral body using the inserter handle, the actuator handle is turned causing the energy storage container to release its energy and drive the actuation rod to expand or compress the implant disposed at a distal end of the inserter locking tube.

2. The system according to claim 1, wherein the inserter handle includes a locking mechanism for interlocking the inserter locking tube to the inserter handle.

3. The system according to claim 1, wherein the actuator handle includes a stopping mechanism configured to prevent turning of the actuator handle past a predetermined angle.

4. The system according to claim 1, wherein the inserter locking tube is configured to accommodate different size and shape implants.

5. The system according to claim 1, wherein the implant is plastically deformable.

6. The system according to claim 1, wherein upon insertion of the implant, the implant is configured to be compressed by the release of energy by rotating the actuator handle in a counterclockwise direction and repositioned within the vertebral body.

7. The system according to claim 1, further comprising a cannula through the inserter locking tube.

8. The system according to claim 7, wherein the cannula can be configured to allow delivery of a bone cement.

9. The system according to claim 1, wherein the energy storage container further comprises a preloaded spring disposed within the energy storage container in a compressed state.

10. The system according to claim 1, wherein the energy storage container is detachable.

11. The system according to claim 1, wherein the energy storage container is reusable.

12. The system according to claim 1, wherein the actuation handle further comprises a screw or linear ratchet mechanism to control the displacement of the actuation rod and the compression and expansion of the implant.

13. The system according to claim 12, wherein the screw is comprises one of a metal material and a plastic material.

14. The system according to claim 1, wherein the implant has a coupling mechanism selected from the group consisting of bayonet connection, "J" shaped, Y-turn, saw-tooth and threaded screw connection.

15. The system according to claim 1, wherein the actuation rod is cannulated.

* * * * *